United States Patent
Uemoto et al.

(10) Patent No.: US 9,934,938 B2
(45) Date of Patent: Apr. 3, 2018

(54) FOCUSED ION BEAM APPARATUS, METHOD FOR OBSERVING CROSS-SECTION OF SAMPLE BY USING THE SAME, AND STORAGE MEDIUM

(71) Applicant: HITACHI HIGH-TECH SCIENCE CORPORATION, Minato-ku, Tokyo (JP)

(72) Inventors: Atsushi Uemoto, Tokyo (JP); Xin Man, Tokyo (JP); Tatsuya Asahata, Tokyo (JP)

(73) Assignee: HITACHI HIGH-TECH SCIENCE CORPORATION (JP)

( * ) Notice: Subject to any disclaimer, the term of this patent is extended or adjusted under 35 U.S.C. 154(b) by 0 days.

(21) Appl. No.: 14/224,164

(22) Filed: Mar. 25, 2014

(65) Prior Publication Data
US 2014/0291508 A1 Oct. 2, 2014

(30) Foreign Application Priority Data
Mar. 28, 2013 (JP) ................... 2013-068169

(51) Int. Cl.
H01J 37/04 (2006.01)
H01J 37/28 (2006.01)
H01J 37/22 (2006.01)
G01N 23/225 (2018.01)

(52) U.S. Cl.
CPC .......... *H01J 37/28* (2013.01); *G01N 23/2255* (2013.01); *H01J 37/222* (2013.01); *G01N 2223/045* (2013.01); *H01J 2237/226* (2013.01); *H01J 2237/24585* (2013.01);
(Continued)

(58) Field of Classification Search
USPC ...................................... 250/492.1
See application file for complete search history.

(56) References Cited

U.S. PATENT DOCUMENTS 6,649,919 B2* 11/2003 Chao .................. H01J 37/3005
250/309
6,670,610 B2* 12/2003 Shemesh et al. ................. 850/9
(Continued)

FOREIGN PATENT DOCUMENTS

JP 8115699 5/1996
JP 11273613 10/1999
(Continued)

OTHER PUBLICATIONS

Notification of Reasons for Refusal dated Sep. 5, 2016 issued in Japanese Patent Application No. 2013-068169 together with English translation thereof.

*Primary Examiner* — Phillip A Johnston
(74) *Attorney, Agent, or Firm* — Bruce L. Adams; Klintworth & Rosenblat IP LLP

(57) ABSTRACT

A focused ion beam apparatus includes a focused ion beam irradiation mechanism that forms first and second cross-sections in a sample. A first image generation unit generates respective first images, either reflected electron images or secondary electron images, of the first and second cross-sections, and a second image generation unit generates a second image that is an EDS image of the first cross-section. A control section generates a three-dimensional image of a specific composition present in the sample based on the first images and the second image.

6 Claims, 6 Drawing Sheets

(52) U.S. Cl.
CPC .......... *H01J 2237/2804* (2013.01); *H01J 2237/2806* (2013.01); *H01J 2237/2807* (2013.01)

(56) References Cited

U.S. PATENT DOCUMENTS

| | | | | |
|---|---|---|---|---|
| 7,138,628 | B2* | 11/2006 | Tomimatsu | G01N 1/28 250/306 |
| 7,154,106 | B2* | 12/2006 | Oi | H01J 37/28 250/311 |
| 7,326,942 | B2* | 2/2008 | Shichi | H01J 27/10 250/492.2 |
| 7,453,274 | B1* | 11/2008 | Zhong | G01N 23/225 250/310 |
| 8,481,980 | B2* | 7/2013 | Shichi | H01J 27/10 250/288 |
| 8,923,614 | B2* | 12/2014 | Itai | G06K 9/4647 382/169 |
| 2009/0020698 | A1 | 1/2009 | Muto et al. | 250/310 |
| 2012/0043463 | A1 | 2/2012 | Agemura et al. | 250/310 |
| 2012/0273692 | A1 | 11/2012 | Tokuda et al. | 250/400 |
| 2014/0076717 | A1* | 3/2014 | Nanri | H01J 37/244 204/192.33 |

FOREIGN PATENT DOCUMENTS

| | | |
|---|---|---|
| JP | 11273936 | 10/1999 |
| JP | 2002150990 | 5/2002 |
| JP | 2009026621 | 2/2009 |
| JP | 2009295371 | 12/2009 |
| JP | 2010257855 | 11/2010 |

* cited by examiner

FOCUSED ION BEAM APPARATUS, METHOD FOR OBSERVING CROSS-SECTION OF SAMPLE BY USING THE SAME, AND STORAGE MEDIUM

CROSS-REFERENCE TO RELATED APPLICATIONS

This application claims priority from Japanese Patent Application No. 2013-068169 filed on Mar. 28, 2013, the entire contents of which are incorporated herein by reference.

TECHNICAL FIELD

Aspect of the present invention relate to a focused ion beam apparatus that observes a sample by subjecting the sample to cross-section processing with a focused ion beam, a method for observing a cross-section of a sample by using the same, and a storage medium storing a computer program for observing a cross-section of a sample by using a focused ion beam.

BACKGROUND

For example, in order to observe defects, impurities and the like of the interior of a semiconductor device, a cross-section for observation is obtained by subjecting a sample to etching processing by using a focused ion beam (FIB) apparatus. As such a method, a technology known as "cut and see" in which the cross-section processing and observation are repeatedly performed is known (for example, see JP-A-H11-273613 and JP-A-H11-273936). Cut and see uses an FIB-SEM apparatus in which a scanning electron microscope (SEM) column is mounted to an FIB apparatus, and is executed by repeating the cross-section processing with the FIB apparatus and acquiring of SEM images of the cross-sections. By combining the plurality of acquired cross-sectional SEM images, it is possible to construct a three-dimensional image of the interior of the sample.

Here, the cross-sectional SEM image is generated by detecting secondary electrons that are emitted by irradiating the cross-section of the sample with a charged particle beam from the SEM column.

Incidentally, characteristic X-rays are emitted in addition to the above-described secondary electrons when an electron beam is emitted from the SEM column to the cross-section of the sample. It is possible to generate an elemental analysis image of the cross-section by detecting the X-rays. This is referred to as energy dispersive X-ray spectrometry (EDS or EDX). Accordingly, by applying the cut and see method to EDS, it is possible to construct a three-dimensional element distribution of the interior of a sample.

SUMMARY

However, because EDS takes time for detection, there is a problem in which the detection time becomes long when EDS images are acquired for all of the cross-sections.

The invention is made to solve the above-described problem, and an object thereof is to provide a focused ion beam apparatus capable of obtaining a region representing a specific composition of the interior of a sample in a short time, a method for observing a cross-section of a sample by using the same, and a storage medium storing a computer program for observing a cross section of a sample by using a focused ion beam.

According to an aspect of the invention, there is provided a focused ion beam apparatus including: a focused ion beam irradiation mechanism configured to irradiate a sample with a focused ion beam so as to form: a first cross-section; and a plurality of second cross-sections at predetermined intervals from the first cross-section and substantially parallel to the first cross-section, the second cross-sections being formed by subjecting the sample to removal processing; a charged particle beam column configured to irradiate the first cross-section and the second cross-section with a charged particle beam; a first detector configured to detect reflected particles or secondary electrons emitted due to irradiation of the charged particle beam on the first cross-section and the second cross-section; a first image generation unit configured to generate a first image of the first cross-section and the second cross-section based on data detected by the first detector, the first image including a reflected electron image or a secondary electron image; a second detector configured to detect X-rays or secondary ions emitted due to irradiation of the charged particle beam on the first cross-section and the second cross-section; a second image generation unit configured to generate a second image of the first cross-section and the second cross-section based on data detected by the second detector, the second image including an EDS image or a secondary ion image; and a control section configured to cause the second image generation unit to generate the second image of the second cross-section, in a case where the first image and the second image of the first cross-section are acquired, the first image of the second cross-section is acquired, and the first image of the second cross-section includes a region different from a region representing a specific composition in the first image of the first cross-section.

According to the focused ion beam apparatus, it is possible to obtain the region representing the specific composition of the interior of a sample in a short time because, instead of operating a second detector which requires time for detecting the specific composition, the region of the cross-section (interior) of the sample is measured by using the first image in place of the region representing the specific composition.

According to another aspect of the invention, there is provided a method for observing a cross-section of a sample by using a focused ion beam, the method including: irradiating a sample with a focused ion beam so as to form: a first cross-section; and a plurality of second cross-sections at predetermined intervals from the first cross-section and substantially parallel to the first cross-section, the second-cross section being obtained by subjecting the sample to a removal processing; irradiating the first cross-section and the second cross-section with a charged particle beam; detecting reflected particles or secondary electrons emitted due to irradiation of the charged particle beam on the first cross-section and the second cross-section; generating a first image of the first cross-section and the second cross-section based on the detected reflected particles or secondary electrons, the first image including a reflected electron image or a secondary electron image; detecting X-rays or secondary ions emitted due to irradiation of the charged particle beam on the first cross-section and the second cross-section; and generating a second image of the first cross-section and the second cross-section based on the detected X-rays or secondary ions, the second image including an EDS image or a secondary ion image, wherein the second image of the second cross-section is generated, in a case where the first image and the second image of the first cross-section are acquired, the first image of the second cross-section is acquired, and the first image of the second cross-section includes a region different from a region representing a specific composition in the first image of the first cross-section.

According to another aspect of the invention, there is provided a non-transitory computer-readable storing medium having a computer program for observing a cross-section of a sample by using a focused ion beam stored thereon and readable by a computer, the computer program, when executed by the computer, causing the computer to perform operations including: irradiating a sample with a focused ion beam so as to form: a first cross-section; and a plurality of second cross-sections at predetermined intervals from the first cross-section and substantially parallel to the first cross-section, the second-cross section being obtained by subjecting the sample to a removal processing; irradiating the first cross-section and the second cross-section with a charged particle beam; detecting reflected particles or secondary electrons emitted due to irradiation of the charged particle beam on the first cross-section and the second cross-section; generating a first image of the first cross-section and the second cross-section based on the detected reflected particles or secondary electrons, the first image including a reflected electron image or a secondary electron image; detecting X-rays or secondary ions emitted due to irradiation of the charged particle beam on the first cross-section and the second cross-section; and generating a second image of the first cross-section and the second cross-section based on the detected X-rays or secondary ions, the second image including an EDS image or a secondary ion image, wherein the second image of the second cross-section is generated, in a case where the first image and the second image of the first cross-section are acquired, the first image of the second cross-section is acquired, and the first image of the second cross-section includes a region different from a region representing a specific composition in the first image of the first cross-section.

Accordingly, it is possible to obtain a region representing a specific composition of the interior of a sample in a short time using a focused ion beam apparatus.

DETAILED DESCRIPTION

Hereinafter, embodiments of the invention will be described with reference to the drawings.

Figure 1:
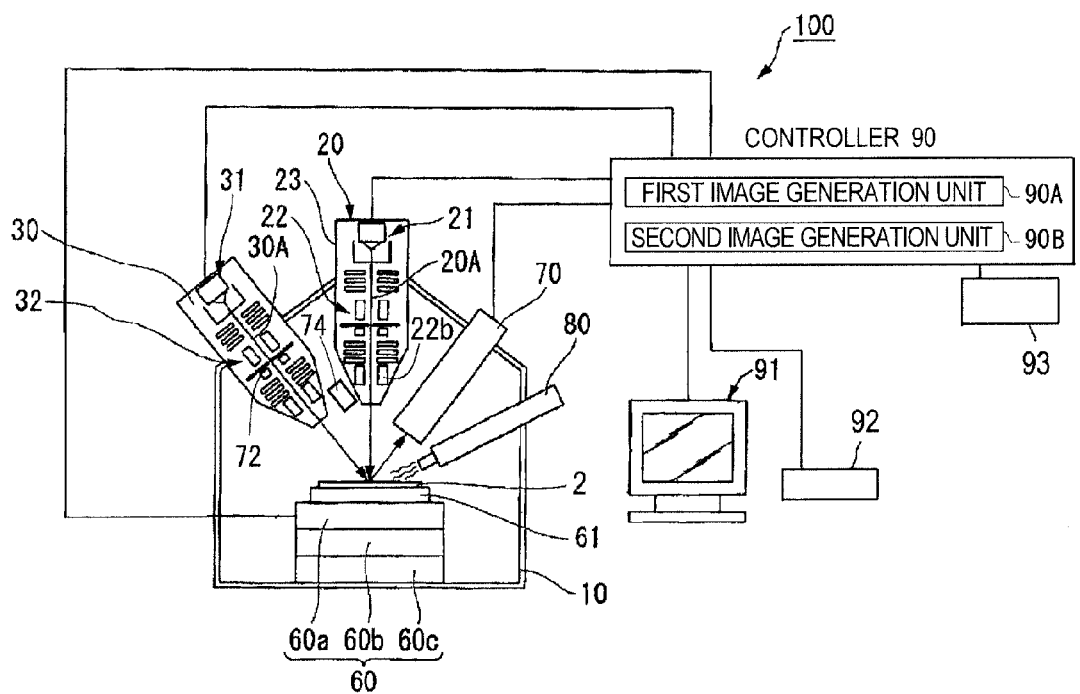
FIG. 1 is a block diagram showing an overall configuration of a focused ion beam apparatus according to an embodiment of the invention.

FIG. 1 is a block diagram showing an overall configuration of a focused ion beam apparatus 100 according to an embodiment of the invention. In FIG. 1, the focused ion beam apparatus 100 includes a vacuum chamber 10, an ion beam irradiation system ("focused ion beam irradiation mechanism" of the claims) 20, a charged particle beam irradiation system ("charged particle beam column" of the claims) 30, a sample stage 60, a secondary charged particle detector 70, a reflected particle detector ("first detector" of the claims) 72, an energy dispersive X-ray spectrometry (EDS) detector ("second detector" of the claims) 74, a gas gun 80, and a controller 90. The pressure is reduced in the interior of the vacuum chamber 10 to a predetermined degree of vacuum, and a portion or all of each constituent part of the focused ion beam apparatus 100 is arranged in the vacuum chamber 10.

In the example hereinafter, a case in which an electron beam column 30 is used as the charged particle beam column, and an electron beam 30A is used as the charged particle beam will be described.

The sample stage 60 movably supports a sample stand 61, and a sample 2 is placed on the sample stand 61. The sample stage 60 has a moving mechanism by which the sample stand 61 is able to be displaced on five axes. The moving mechanism includes an XYZ moving mechanism 60b that moves the sample stand 61 along an X-axis and a Y-axis that are parallel to the horizontal plane and orthogonal to each other, and a Z-axis that is orthogonal to the X-axis and the Y-axis, a rotation mechanism 60c that rotates the sample stand 61 around the Z-axis, and a tilting mechanism 60a that rotates the sample stand 61 around the X-axis (or the Y-axis). The sample stage 60 moves the sample 2 to the irradiation position of the ion beam 20A by displacing the sample stand 61 in the five axes.

The controller 90 may be configured by a computer including a CPU as a central calculation processing device, a storage portion (RAM and ROM) 93 that stores data, programs and the like, and an input port and an output port that perform input and output of signals with an external device. The controller 90 causes the CPU to execute various calculation processes based on a program stored in the storage portion 93, and controls each constituent part of the focused ion beam apparatus 100. The controller 90 is electrically connected to the control wirings or the like of the ion beam (hereinafter, focused ion beam is shorted to "ion beam", as appropriate) irradiation system 20, the charged particle beam irradiation system 30, the secondary charged particle detector 70, the reflected particle detector 72, the EDS detector 74 and the sample stage 60.

The controller 90 includes a first image generation unit 90A and a second image generation unit 90B.

Additionally, the controller 90 drives the sample stage 60 based on software commands or operator input, and is able to adjust the irradiation position and the irradiation angle of the ion beam 20A on the surface of the sample 2 by adjusting the position and posture of the sample 2.

An input unit 92, such as a keyboard that receives operator input instructions, is connected to the controller 90.

The controller 90 controls the irradiation of the ion beam 20A by controlling the sample stage 60, an ion source 21, and the ion beam irradiation system optical system 22. The controller 90 controls a deflector 22b and the irradiation conditions of the ion beam 20A, along with controlling the output of the ion beam 20A emitted from the ion source 21. The controller 90 performs a removal processing on a predetermined portion of the sample 2 by irradiating the sample with the ion beam 20A while moving the sample stage 60.

Figure 2:
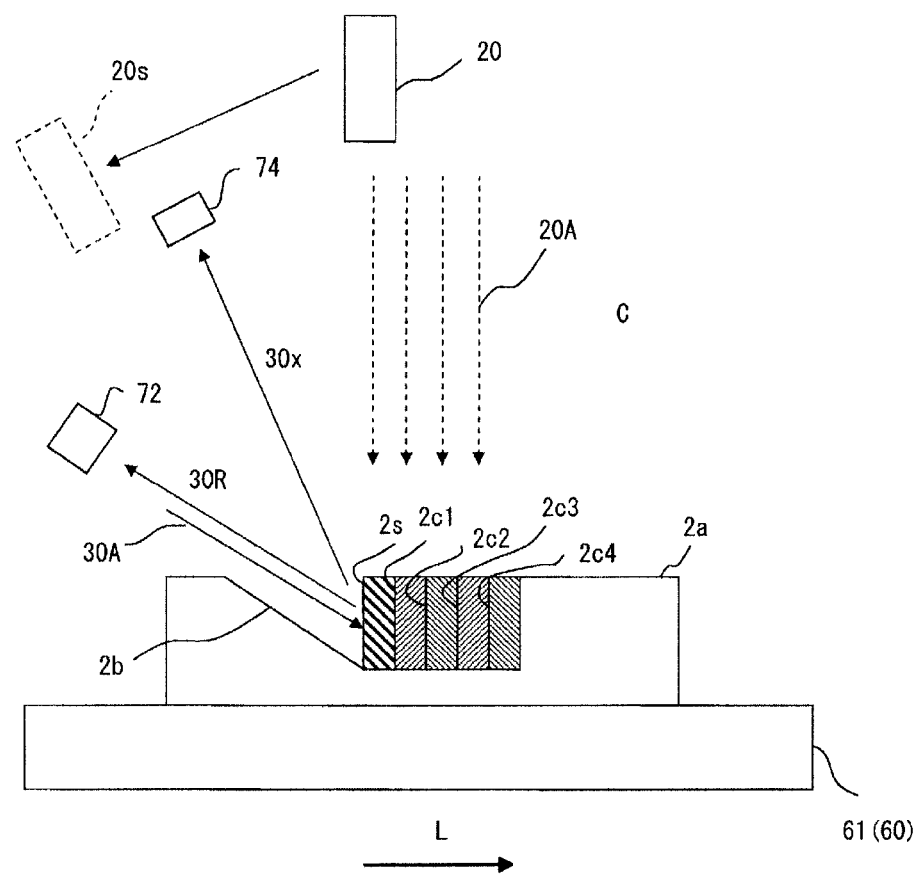
FIG. 2 is a diagram showing a method for performing removal processing.

The removal processing is performed as in, for example, FIG. 2. First, the sample 2 is removed in a trench form (groove form) in the depth direction by irradiating the surface 2a of the sample 2 with the ion beam 20A perpendicularly, and an inclined surface 2b that inclines from the surface is formed. A surface that rises perpendicularly from the inclined surface 2b towards the surface 2a becomes the first cross-section 2s of the sample. The first cross-section 2s is irradiated with an electron beam 30A from a direction inclined to the surface 2a, and X-rays emitted due to the irradiation are detected with the EDS detector 74, along with detecting the reflected electrons thereof with the reflected particle detector 72.

Next, the ion beam 20A is moved in the direction L (from left to right in FIG. 2), the sample including the first cross-section 2s is removed, and a second cross-section 2c1 substantially parallel to the first cross-section 2s is formed on the right side of the first cross-section 2s at a predetermined interval. Hereinafter, the sample is removed each time the ion beam 20A moves in the direction L, and second cross-sections 2c2 to 2c4 parallel to the second cross-section 2c1 are sequentially formed.

The reflected particle detector 72 detects reflected electrons 30R that are emitted due to the irradiation of the electron beam 30A from the charged particle beam column 30 to the first cross-section 2s and each of the second cross-sections 2c1 to 2c4 of the sample 2 (see FIG. 2).

The first image generation unit 90A generates reflected electron images ("first image" of the claims) of the first cross-section 2s and the second cross-sections 2c1 to 2c4 based on data detected by the reflected particle detector 72.

Incidentally, it is possible to form a secondary electron image by detecting secondary electrons, which are emitted due to irradiation of the electron beam 30A from the charged particle beam column 30 to the first cross-section 2s and each second cross-section 2c1 to 2c4, with the secondary charged particle detector 70, and use this secondary electron image as the first image.

The controller 90 sets the contrast that corresponds to a region representing a specific composition appearing in the reflected electron image as an initial value. Here, in the reflected electron image, as the atomic number increases, more reflected electrons are emitted, and as the product of atomic number and density increases (as the element becomes heavier), the contrast becomes brighter (see FIG. 6 described later). Accordingly, the contrast of the reflected electron image represents characteristics (type of element, crystal orientation or the like) in which the atomic number or the density is reflected. The contrast of the reflected electron image is converted to a numerical value by dividing the brightness of the image in a step-wise manner. Since the reflected electron image is a black and white image, it is possible to stipulate a grayscale value that defines the grayscale value of white as 256 and the grayscale value of black as 1, and each pixel corresponds to a predetermined grayscale value. Considering errors and the like, the contrast as the initial value may be set to have a width of numerical values of a given extent and not one point of grayscale value. For example, when the initial value is set to 100, the initial value is able to have a width of 90 to 110.

The contrast setting may be set by an operator designating an arbitrary region on the reflected electron image of the first cross-section 2s by operating the input unit 92. In a case in which the arbitrary region includes a plurality of pixels, the method for determining the contrast of the region is not particularly limited, and for example, an average value of the grayscale values of the pixels thereof may be set as the contrast, or the largest value among the grayscale value of each pixel may be set as the contrast. Further, when the operator selects one point (one pixel) in the region, a plurality of pixels of a predetermined region on the periphery thereof may be automatically acquired so as to set the contrast.

It is possible to set the initial value on the reflected electron image of the first cross-section 2s. In this case, for example, after the operator confirms the region representing the characteristics of the first cross-section 2s on the second image showing the characteristics (described later), the contrast in the vicinity of the region of a position corresponding to the second image on the reflected electron image of the first cross-section 2s is set (see FIG. 3A). More specifically, examples include cases in which impurities (for example, magnesium) in the cross-section of a semiconductor sample are discovered on, for example, the second image, and the contrast corresponding to the position thereof is set on the reflected electron image.

Meanwhile, the contrast may be set as an initial value without observing the reflected electron image of the first cross-section 2s. For example, the operator may input and set a grayscale value by operating the input unit 92. This case corresponds to a case in which, for example, impurities (for example, the above-described magnesium) used as an objective in the semiconductor device sample are known in advance, and the contrast of the impurities on the reflected electron image is also known in advance. In this case, instead of inputting a grayscale value, when an operator designates the type of impurity on a predetermined screen, it is possible to make the grayscale value corresponding to the impurities to be automatically designated.

The EDS detector 74 detects characteristic X-rays 30x that are emitted due to irradiation of the electron beam 30A from the charged particle beam column 30 to the first cross-section 2s of the sample 2 and a predetermined second cross-section 2c4 (see FIG. 2).

The second image generation unit 90B generates an EDS image ("second image" of the claims) of the first cross-section 2s and the second cross-section 2c4 based on data detected by the EDS detector 74. In the EDS (or EDX) image, it is possible to know the distribution of the elements in the sample based on the fact that the energies (wavelength) of the characteristic X-rays differ according to the type of element. It is possible to make the elements (impurities or the like) on the EDS image as described above to correspond to the contrast on the reflected electron image by observing the EDS image of the first cross-section 2s.

The reflected electron image and the EDS image are output to a display device (display) 91 connected to the controller 90 and are stored in the storage portion 93 as image data (bitmap data).

The controller 90 controls the operation of the EDS detector 74. Because time is taken to obtain one EDS image because the sensitivity of the EDS detector 74 is low, the detection time increases if EDS images are acquired for all of the second cross-sections 2c1 to 2c4. Therefore, the controller 90 controls the operation of the EDS detector 74 so as to acquire only the necessary EDS images.

The ion beam irradiation system 20 includes an ion source 21 in which ions are generated and an ion beam optical system 22 in which ions discharged from the ion source 21 are formed into a focused ion beam and scanned. The sample 2 on the sample stage 60 in the vacuum chamber 10 is irradiated with the ion beam 20A that is a charged particle beam from the ion beam irradiation system 20 that includes the ion beam column 23. At this time, secondary charged particles, such as secondary ions and secondary electrons are emitted from the sample 2. An image of the sample 2 is acquired by detecting these secondary charged particles with the secondary charged particle detector 70. The ion beam irradiation system 20 performs etching processing (removal processing) on the sample 2 in the irradiation range by increasing the irradiation amount of the ion beam 20A.

The ion beam optical system 22 is configured to include, for example, a condenser lens that focuses the ion beam 20A, a diaphragm that narrows the ion beam 20A, an aligner that adjusts the optical axis of the ion beam 20A, an object lens that focuses the ion beam 20A on the sample, and a deflector 22b that scans the ion beam 20A on the sample.

The charged particle beam irradiation system 30 includes an electron source 31 that emits electrons, and an electron optical system 32 in which electrons emitted from the electron source 31 are formed into a beam and scanned. Reflected electrons and X-rays emitted from the sample 2 according to the irradiation of the electron beam 30A from the charged particle beam irradiation system 30 on the sample 2 are respectively detected by the particle detector 72 and the EDS detector 74, and it is possible to acquire a reflected electron image and an EDS image of the sample 2 as described above.

The secondary charged particle detector 70 detects secondary charged particles (secondary electrons or secondary ions) emitted from the sample 2 when the sample 2 is irradiated with the ion beam 20A or the electron beam 30A.

The gas gun 80 discharges a predetermined gas, such as an etching gas, on the sample 2. By irradiating the sample 2 with the ion beam 20A while supplying the etching gas from the gas gun 80, it is possible to increase the etching speed of the sample with the ion beam 20A. In addition, by irradiating the sample 2 with the ion beam 20A while supplying a compound gas from the gas gun 80, it is possible to precipitate (deposition) topical gas components in the vicinity of the irradiation region of the ion beam 20A.

Next, the generation of the reflected electron image and the EDS by the focused ion beam apparatus 100 according to the embodiment of the invention will be described with reference to FIGS. 3 to 9. First, a first cross-section 2s of the sample (semiconductor device) is formed as shown in FIG. 2.

FIG. 3 shows a procedure that generates a reflected electron image and an EDS image for the first cross-section 2s and each of the second cross-sections 2c1 to 2c4. First, a reflected electron image Gs and an EDS image Hs are generated for the first cross-section 2s (FIG. 3A). Then, the operator confirms the region NH of the impurities (for example, magnesium), which is an observation target, on the EDS image Hs, as described above. Next, the operator sets the contrast of the region ("region representing the specific composition" of the claims) N of the position corresponding to the EDS image Hs to the initial value on the reflected electron image Gs.

Figure 3A:
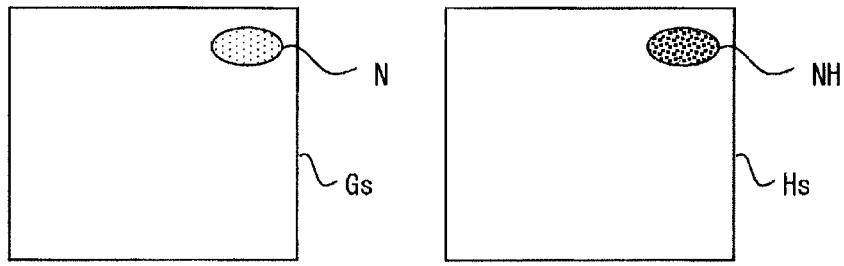
FIG. 3 (3A to 3E) is a diagram showing a procedure that generates a reflected electron image and an EDS image at a first cross-section and each second cross-section.
Figure 3B:
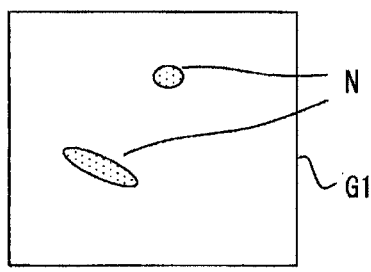
Figure 3C:
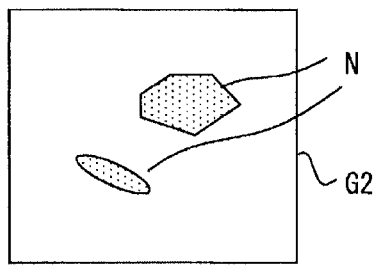
Figure 3D:
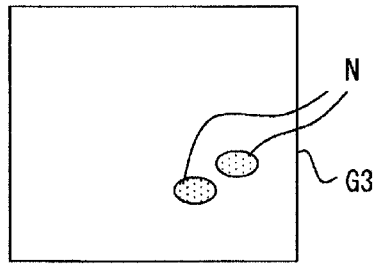

Next, the reflected electron image G1 is generated for the second cross-section 2c1 (FIG. 3B). In the reflected electron image G1, since the region N having contrast of the initial value set in FIG. 3A is present, the EDS image is not generated. Then, the reflected electron images G2 and G3 are similarly generated for the second cross-sections 2c2 and 2c3 (FIGS. 3C and 3D). Also in each of the reflected electron images G2 and G3, since the region N having contrast of the initial value set in FIG. 3A is present, the EDS image is not generated.

Figure 3E:
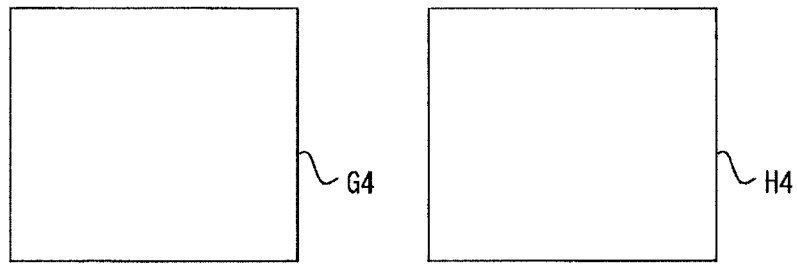

Next, the reflected electron image G4 is generated for the second cross-section 2c4 (FIG. 3E). In the reflected electron image G4, the region N having contrast of the initial value set in FIG. 3A disappears. Since this means a reflected electron image having different contrast (region different from the region representing the specific composition) from the initial value (different type of reflected electron image), the EDS image H4 is generated. In the EDS image H4, it is possible to confirm that impurities (magnesium) are not present.

Figure 4:
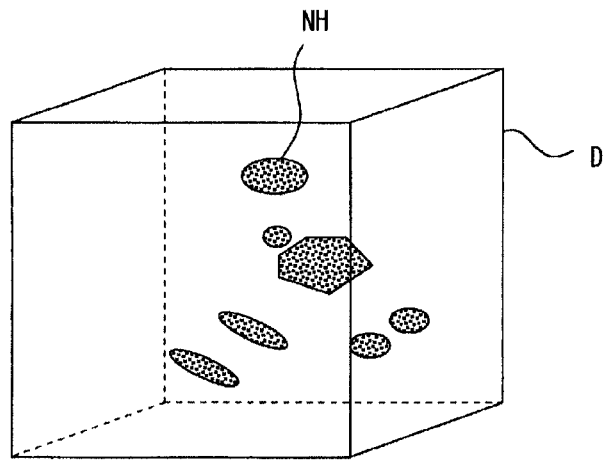
FIG. 4 is a diagram showing a three-dimensional distribution pattern of a specific composition.

Next, as shown in FIG. 4, a three-dimensional distribution pattern D of the impurities (magnesium) is generated based on the reflected electron images G1 to G4 and the EDS image Hs. More specifically, the regions N in the reflected electron images G1 to G4 are taken as the region NH on the EDS image, and the reflected electron images G1 to G4 and the EDS image Hs are arranged in time-series order, thereby generating a three-dimensional distribution pattern D of the region NH.

In this way, when measuring the presence or absence of impurities (magnesium) of the sample cross-section and generating a three-dimensional distribution pattern thereof, since only the necessary EDS image Hs may be acquired, it is possible to reduce the length of the detection time compared to a case of acquiring an EDS image with respect to all of the second cross-sections 2c1 to 2c4.

Further, even in a case in which the processing is finished in FIG. 3E without generating the three-dimensional distribution pattern shown in FIG. 4, it is possible to rapidly know up to which cross-section position (second cross-section 2c3) are the impurities (magnesium) present. Therefore, the length of the detection time can be reduced compared to a case of acquiring an EDS image with respect to all of the second cross-sections 2c1 to 2c4.

Figure 5:
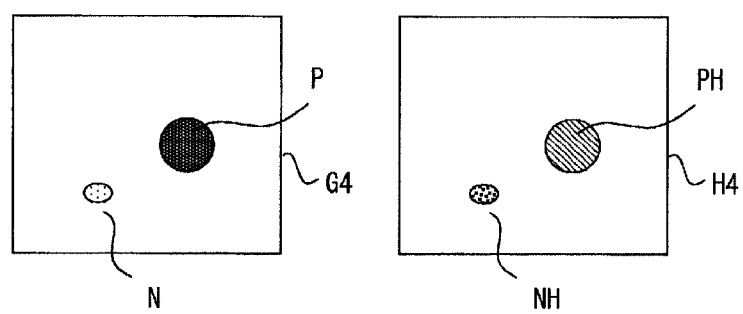
FIG. 5 is a diagram showing another image of FIG. 3E.

FIG. 5 shows another image of FIG. 3E. In FIG. 5, on the reflected electron image G4, in addition to the region N having contrast set in FIG. 3A, a case is assumed in which a region P having a contrast different from the region N appears. Because the region P represents different elements to the region N, the EDS image H4 is generated for the second cross-section 2c4, and the composition of the elements of the region PH corresponding to the region P is confirmed.

In this case, the contrast of the region P is updated as the initial value, and EDS images are not generated until a reflected electron image (different type of reflected electron image) having contrast different from the initial value (contrast of the region P) is next discovered in subsequent second cross-sections further obtained by removal processing on the sample 2 from the second cross-section 2c4.

By doing so, similarly to the above description, it is possible to rapidly know up to which cross-section position (second cross-section) are the elements of the region P are present and it is possible to rapidly generate a three-dimensional distribution pattern of the elements of region P.

In FIG. 5, even in a case where the region N disappears and the region P appears instead on the reflected electron image G4, similarly procedure as described above will be performed.

Figure 6:
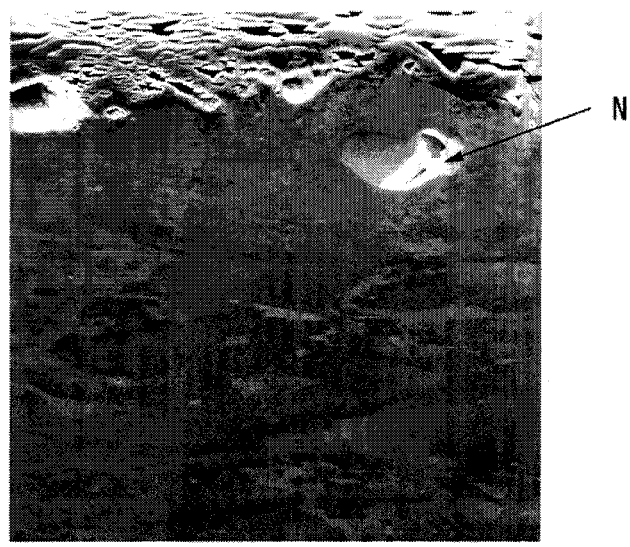
FIG. 6 is a diagram showing a reflected electron image and an EDS image in a first cross-section of an actual semiconductor device sample.

FIG. 6 shows a reflected electron image Gs in the first cross-section 2s of a practical semiconductor device sample. The region N on the reflected electron image Gs represents the impurities (magnesium).

Figure 7:
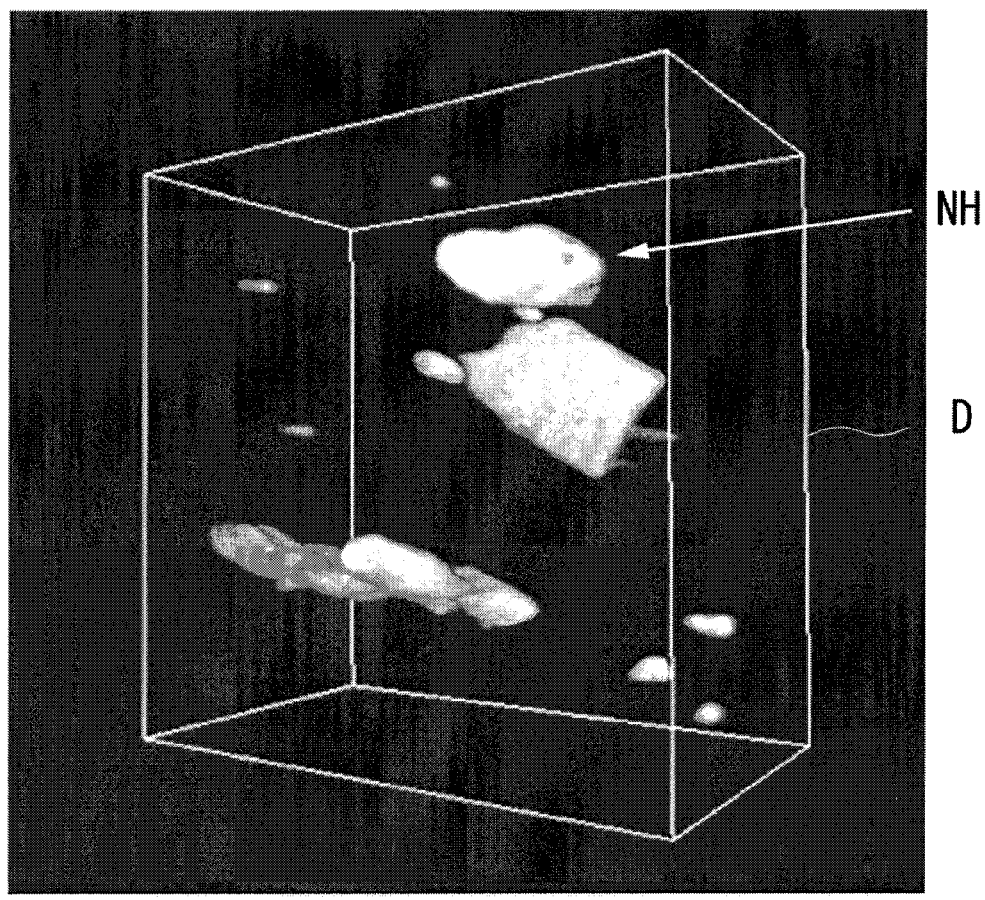
FIG. 7 is a diagram showing an actual three-dimensional distribution pattern of a specific composition in which the reflected electron image and the EDS image of FIG. 6 are used.

FIG. 7 shows a three-dimensional distribution pattern D of practical impurities (magnesium) in which the reflected electron image in FIG. 6 and EDS images (not shown in the drawings) acquired corresponding to a reflection image are used.

Figure 8:
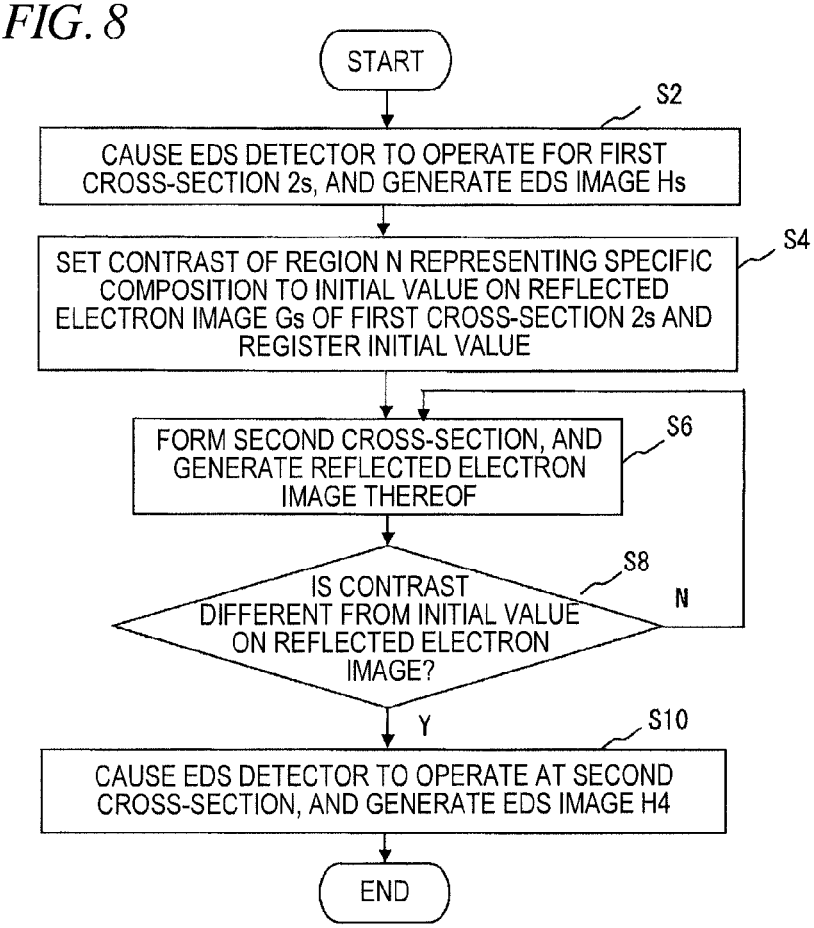
FIG. 8 is a diagram showing a flow of the process shown by FIG. 3.

Next, the flow of the process shown by FIG. 3 will be described with reference to FIG. 8. First, the controller 90 causes the EDS detector 74 to operate for the first cross-section 2s, and the second image generation unit 90B generates the EDS image Hs based on the data detected by the EDS detector 74 (Step S2). The operation in Step S2 may be performed by an operator, on a task setting screen on the display device 91, causing software that performs processing of the main apparatus to activate.

Next, while referring to the region NH of the impurities (magnesium) of the EDS image Hs, on the reflected electron image Gs of the first cross-section 2s, when the operator designates the region N by operating the input unit 92, the controller 90 acquires (sets) the contrast of the region N representing the specific composition as an initial value, and registers this in the storage portion 93 (Step S4).

After Step S4, the controller 90 forms the second cross-section 2c1 as shown in FIG. 2. The first image generation unit 90A generates the reflected electron image G1 of the second cross-section 2c1 based on the data detected by the reflected particle detector 72 (step S6).

Next, the controller 90 determines whether or not a contrast different from the initial value is present on the reflected electron image G1 (that is, whether or not "includes a region different from a region representing a specific composition") (Step S8). If Step S8 is "No", the process returns to Step S6, and the next second cross-section 2c2 (to 2c3) is formed, and the reflected electron image G2 (to G3) of the second cross-section thereof is generated. If Step S8 is "Yes", the process transitions to Step S10. Hereinafter, a case in which Step S8 is "Yes" for the reflected electron image G2 of the second cross-section 2c4 will be described as an example.

In Step S10, the controller 90 causes the EDS detector 74 to operate for the second cross-section 2c4, and the second image generation unit 90B generates the EDS image H4 based on the data detected by the EDS detector 74.

Figure 9:
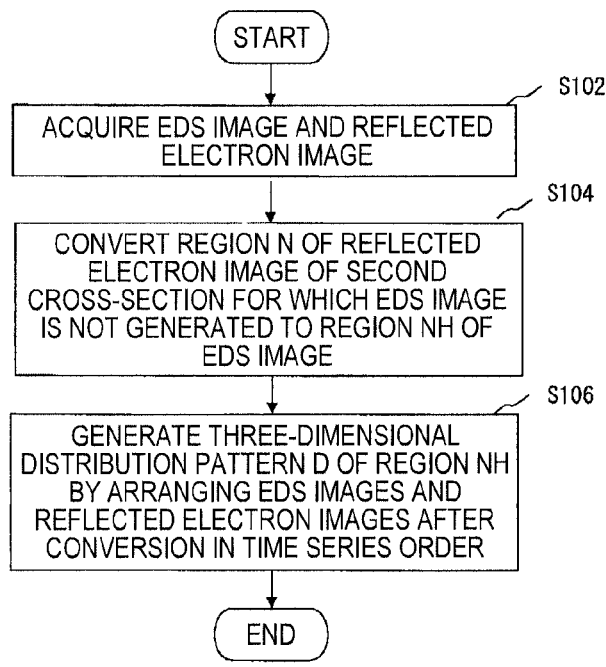
FIG. 9 is a diagram showing a flow of the process shown by FIG. 4.

Next, the flow of the process in FIG. 4 will be described with reference to FIG. 9. The controller 90 acquires the image data of the reflected electron images G1 to G3 and the EDS image Hs of the first cross-section from the storage portion 93 (Step S102).

Next, the controller 90 converts the region N representing the specific composition in the reflected electron images G1 to G3 of the second cross-sections 2c1 to 2c3 for which the EDS image Hs is not generated to the region NH of the EDS image (Step S104). The conversion in Step S104 is performed by converting the contrast of the region N to the contrast represented by the region NH.

The controller 90 arranges the EDS image Hs and the reflected electron images G1 to G3 after conversion in Step S104 in time series order (see FIG. 2), and generates the three-dimensional distribution pattern D of the region NH on the EDS image (Step S106).

The present invention is not limited to the above-described embodiments, and it goes without saying that making various modifications and substitutions are included within the scope of the invention.

For example, the contrast set as an initial value is not limited to the above as long as it corresponds to the predetermined characteristics of the reflected electron image. Specific elements and orientation are examples of the characteristics.

In addition, the second detector is not limited to the above as long as it is able to analyze the predetermined characteristics of the reflected electron image.

In a case in which an element species is employed as the characteristic, when the secondary charged particle detector 70 is used instead of the above EDS detector 74, and the sample 2 is irradiated with the ion beam 20A, it is possible to detect the secondary ions emitted from the sample 2. Additionally, it is possible to use the reflected particle detector 72 and detect the reflected ions reflected from the sample 2. However, in this case, when generating a composition image of the first cross-section and the second cross-section, it is necessary to incline the sample stage 60 so that the focused ion beam irradiation mechanism 20 relatively moves from the position directly above the sample 2 to the position 20s of the broken line as shown in FIG. 2.

Further, it is possible to use a focused ion beam irradiation mechanism including a gas field ionization ion source instead of the charged particle beam irradiation system 30. By using a gas field ionization ion source, it is possible to irradiate the first cross-section and the second cross-section with an ion beam with an ion species with a low mass, such as barium or hydrogen, with a narrow beam radius. Accordingly, it is possible to acquire a high resolution reflected ion image or secondary electron image (first image) while reducing the damage to the first cross-section and the second cross-section. The above "focused ion beam irradiation mechanism including a gas field ionization ion source" corresponds to the "charged particle beam column" of the claims. Additionally, the ion beam emitted from the gas field ionization ion source corresponds to the "charged particle beam" of the claims.

What is claimed is:

1. A focused ion beam apparatus comprising:
a focused ion beam irradiation mechanism configured to irradiate a sample with a focused ion beam in a direction perpendicular to the sample surface to form an inclined surface that begins at the sample surface and ends at a depth in the sample and thereafter form at the depth end of the inclined surface a first cross-section and a plurality of second cross-sections at predetermined intervals from the first cross-section and substantially parallel to the first cross-section, the first cross-section and the second cross-sections each beginning at the sample surface and ending at a depth in the sample and being formed by subjecting the sample to removal processing with the focused ion beam;
a charged particle beam column configured to irradiate the first cross-section and the second cross-sections with a charged particle beam;
a first detector configured to detect reflected particles or secondary electrons emitted due to irradiation of the charged particle beam on the first cross-section and the second cross-sections;
a second detector configured to detect X-rays or secondary ions emitted due to irradiation of the charged particle beam on the first cross-section and the second cross-sections; and;
a control section configured to:
generate a first image of the first cross-section and of the second cross-sections based on data detected by the first detector, the first image including a reflected electron image or a secondary electron image;

generate a second image of the first cross-section based on data detected by the second detector, the second image including an EDS image or a secondary ion image of the first cross-section;

determine whether the first image of the second cross-sections includes a region different from a region representing a specific composition in the first image of the first cross-section based on a contrast of the first image;

control the second detector to detect X-rays or secondary ions emitted due to irradiation of the charged particle beam on the second cross-sections when determined that the first image of the second cross-sections includes the region different from the region representing the specific composition in the first image of the first cross-section;

generate a second image of the second cross-sections based on the detected X-rays or secondary ions, the second image including an EDS image or a secondary ion image of the second cross-sections when determined that the first image of the second cross-sections includes the region different from the region representing the specific composition in the first image of the first cross-section;

generate a second image of the second cross-sections, when not determined that the first image of the second cross-sections includes the region different from the region representing the specific composition in the first image of the first cross-section, based on the first image of the first cross-section, the first image of the second cross-sections and the second image of the first cross-section, without controlling the second detector to detect X-rays or secondary ions emitted due to irradiation of the charged particle beam on the second cross-sections; and generate a three-dimensional distribution pattern of a specific composition present in the sample based on the first images and the second images which include the region representing the specific composition.

2. The focused ion beam apparatus according to claim 1, wherein the control section is configured to generate a three-dimensional distribution pattern of the specific composition based on the second image of the first cross-section and a first image of the second cross-section that does not include a region different from the region representing the specific composition.

3. A method for observing a cross-section of a sample that includes a specific composition by using a focused ion beam, the method comprising:

irradiating a sample with a focused ion beam in a direction perpendicular to the sample surface to form an inclined surface that begins at the sample surface and ends at a depth in the sample and thereafter form at the depth end of the inclined surface a first cross-section and a plurality of second cross-sections at predetermined intervals from the first cross-section and substantially parallel to the first cross-section, the first cross-section and the second cross-sections each beginning at the sample surface and ending at a depth in the sample and being obtained by subjecting the sample to a removal processing with the focused ion beam;

irradiating the first cross-section and the second cross-sections with a charged particle beam;

detecting reflected particles or secondary electrons emitted due to irradiation of the charged particle beam on the first cross-section and the second cross-sections;

generating a first image of the first cross-section and of the second cross-sections based on the detected reflected particles or secondary electrons, the first image including a reflected electron image or a secondary electron image;

detecting X-rays or secondary ions emitted due to irradiation of the charged particle beam on the first cross-section;

generating a second image of the first cross-section based on the detected X-rays or secondary ions, the second image including an EDS image or a secondary ion image of the first cross-section;

determining whether the first image of the second cross-sections includes a region different from a region representing the specific composition in the first image of the first cross-section based on a contrast of the first image;

detecting X-rays or secondary ions emitted due to irradiation of the charged particle beam on the second cross-sections when determined that the first image of the second cross-sections includes the region different from the region representing the specific composition in the first image of the first cross-section;

generating a second image of the second cross-sections based on the detected X-rays or secondary ions, the second image including an EDS image or a secondary ion image of the second cross-sections when determined that the first image of the second cross-sections includes the region different from the region representing the specific composition in the first image of the first cross-section;

generating a second image of the second cross-sections, when not determined that the first image of the second cross-sections includes the region different from the region representing the specific composition in the first image of the first cross-section, based on the first image of the first cross-section, the first image of the second cross-sections and the second image of the first cross-section, without controlling the second detector to detect X-rays or secondary ions emitted due to irradiation of the charged particle beam on the second cross-sections; and generating a three dimensional distribution pattern of the specific composition based on the first images and the second images which include the region representing the specific composition.

4. The method for observing a cross-section of a sample by using a focused ion beam according to claim 3, wherein generating a three-dimensional distribution pattern comprises generating a three-dimensional distribution pattern of the specific composition based on the second image of the first cross-section; and a first image of the second cross-section that does not include a region different from the region representing the specific composition.

5. A non-transitory computer-readable storing medium having a computer program for observing a cross-section of a sample that includes a specific composition by using a focused ion beam stored thereon and readable by a computer, the computer program, when executed by the computer, causing the computer to perform operations comprising:

irradiating a sample with a focused ion beam in a direction perpendicular to the sample surface to form an inclined surface that begins at the sample surface and ends at a depth in the sample and thereafter form at the depth end of the inclined surface a first cross-section and a plurality of second cross-sections at predetermined intervals from the first cross-section and substantially parallel to the first cross-section, the first cross-section and the second cross-sections each beginning at the sample surface and ending at a depth in the sample and being obtained by subjecting the sample to a removal processing with the focused ion beam;

irradiating the first cross-section and the second cross-sections with a charged particle beam;

detecting reflected particles or secondary electrons emitted due to irradiation of the charged particle beam on the first cross-section and the second cross-sections;

generating a first image of the first cross-section and of the second cross-sections based on the detected reflected particles or secondary electrons, the first image including a reflected electron image or a secondary electron image;

detecting X-rays or secondary ions emitted due to irradiation of the charged particle beam on the first cross-section;

generating a second image of the first cross-section based on the detected X-rays or secondary ions, the second image including an EDS image or a secondary ion image of the first cross-section;

determining whether the first image of the second cross-sections includes a region different from a region representing the specific composition in the first image of the first cross-section based on a contrast of the first image;

detecting X-rays or secondary ions emitted due to irradiation of the charged particle beam on the second cross-sections when determined that the first image of the second cross-sections includes the region different from the region representing the specific composition in the first image of the first cross-section;

generating a second image of the second cross-sections based on the detected X-rays or secondary ions, the second image including an EDS image or a secondary ion image of the second cross-sections when determined that the first image of the second cross-sections includes the region different from the region representing the specific composition in the first image of the first cross-section;

generating a second image of the second cross-sections, when not determined that the first image of the second cross-sections includes the region different from the region representing the specific composition in the first image of the first cross-section, based on the first image of the first cross-section, the first image of the second cross-sections and the second image of the first cross-section, without controlling the second detector to detect X-rays or secondary ions emitted due to irradiation of the charged particle beam on the second cross-sections; and generating a three-dimension al distribution pattern of the specific composition based on the first images and the second images which include the region representing the specific composition.

6. The non-transitory computer-readable storing medium according to claim 5, the operations further comprising:

generating a three-dimensional distribution pattern of the specific composition based on the second image of the first cross-section and a first image of the second cross-section that does not include a region different from the region representing the specific composition.

* * * * *